United States Patent [19]
Nita

[11] Patent Number: 5,368,558
[45] Date of Patent: * Nov. 29, 1994

[54] ULTRASONIC ABLATION CATHETER DEVICE HAVING ENDOSCOPIC COMPONENT AND METHOD OF USING SAME

[75] Inventor: Henry Nita, Mission Viejo, Calif.

[73] Assignee: Baxter International Inc., Deerfield, Ill.

[*] Notice: The portion of the term of this patent subsequent to Dec. 7, 2010 has been disclaimed.

[21] Appl. No.: 72,203

[22] Filed: Jun. 3, 1993

Related U.S. Application Data

[63] Continuation-in-part of Ser. No. 911,546, Jul. 9, 1992, Pat. No. 5,312,328, which is a continuation-in-part of Ser. No. 878,795, May 5, 1992, Pat. No. 5,267,954, which is a continuation-in-part of Ser. No. 787,292, Nov. 4, 1991, abandoned, which is a continuation-in-part of Ser. No. 640,190, Jan. 11, 1991, Pat. No. 5,304,115.

[51] Int. Cl.$^5$ ............................................. A61B 17/20
[52] U.S. Cl. ........................................ 604/22; 604/52; 601/2
[58] Field of Search ................... 128/24 AA, 898; 606/169–171, 159; 604/21, 22, 49.52; 601/2

[56] References Cited

U.S. PATENT DOCUMENTS

| | | |
|---|---|---|
| 3,352,303 | 11/1967 | Delaney . |
| 3,433,226 | 3/1969 | Boyd . |
| 3,526,219 | 9/1970 | Balamuth . |
| 3,565,062 | 3/1971 | Kuris . |
| 3,589,363 | 6/1971 | Banko . |
| 3,618,594 | 11/1971 | Banko . |
| 3,809,093 | 5/1974 | Abraham . |
| 3,823,717 | 7/1974 | Pohlman . |
| 3,861,391 | 1/1975 | Antonevich et al. . |
| 3,896,811 | 7/1975 | Storz . |
| 4,188,952 | 2/1980 | Loschivlov et al. . |
| 4,214,586 | 7/1980 | Mericle . |
| 4,223,676 | 9/1980 | Wuchinich et al. . |
| 4,366,819 | 1/1983 | Kaster . |
| 4,431,006 | 2/1984 | Trimmer et al. . |
| 4,474,180 | 10/1984 | Angulo . |
| 4,587,958 | 5/1986 | Noguchi et al. . |
| 4,587,972 | 5/1986 | Morantte . |
| 4,589,419 | 5/1986 | Laughlin et al. . |

(List continued on next page.)

FOREIGN PATENT DOCUMENTS 0424231 4/1984 European Pat. Off. .

(List continued on next page.)

OTHER PUBLICATIONS

Circulation, vol. 81, No. 2, Feb. 1990, "Application of a New Phased-Array Ultrasound Imaging Catheter in the Assessment of Vascular Dimensions," pp. 660–666.
"Ultrasonic Energy Causes Doe-Dependent, Endothelium-Independent Arterial Relaxation"—T. Fischell, et al. Abstracts of the 63rd Scientific Sessions, pp. 111-219.

Primary Examiner—C. Fred Rosenbaum
Assistant Examiner—Michael Rafa
Attorney, Agent, or Firm—Stetina & Brunda

[57] ABSTRACT

A catheter device insertable into a body lumen and incorporating combined ultrasound ablation and endoscopic visualization apparatus. The catheter device generally comprises an elongate catheter body including an ultrasound transmission member extending longitudinally therethrough having a proximal end connectable to an ultrasound transducer such that ultrasonic energy will pass through the ultrasound transmission member to the distal end thereof. Also extending longitudinally through the catheter body is a light transmission member having a proximal end connectable to a light source such that light will pass through the light transmission member to the distal end thereof, and an optical image transmission member having a proximal end connectable to an external image viewing apparatus such that an optical image will pass through the optical image transmission member from the distal end thereof to the external image viewing apparatus.

15 Claims, 4 Drawing Sheets

U.S. PATENT DOCUMENTS

| | | |
|---|---|---|
| 4,665,906 | 5/1987 | Jervis . |
| 4,692,139 | 9/1987 | Stiles . |
| 4,750,902 | 6/1988 | Wuchinich et al. . |
| 4,794,931 | 1/1989 | Yock . |
| 4,799,496 | 1/1989 | Hargraves . |
| 4,800,876 | 1/1989 | Fox et al. . |
| 4,808,153 | 2/1989 | Parisi . |
| 4,821,731 | 4/1989 | Marinelli . |
| 4,841,977 | 6/1989 | Griffith . |
| 4,844,092 | 7/1989 | Rydell . |
| 4,867,141 | 9/1989 | Nakada et al. ............... 604/22 |
| 4,870,953 | 10/1989 | DonMichael . |
| 4,898,575 | 2/1990 | Fischell et al. . |
| 4,917,097 | 4/1990 | Proudian et al. . |
| 4,919,133 | 4/1990 | Chiang . |
| 4,920,954 | 5/1990 | Alliger et al. . |
| 4,923,441 | 5/1990 | Shuler . |
| 4,924,863 | 5/1990 | Sterzer . |
| 4,936,281 | 6/1990 | Stasz . |
| 4,957,111 | 9/1990 | Millar . |
| 4,960,411 | 10/1990 | Buchbinder . |
| 4,967,653 | 11/1990 | Hinz . |
| 4,967,753 | 11/1990 | Haase et al. . |
| 4,979,939 | 12/1990 | Shiber . |
| 4,988,356 | 1/1991 | Crittenden . |
| 4,998,527 | 3/1991 | Meyer . |
| 5,022,399 | 6/1991 | Biegeleisen . |
| 5,029,588 | 7/1991 | Yock et al. . |
| 5,058,570 | 10/1991 | Idemoto et al. . |
| 5,061,238 | 10/1991 | Shuler . |
| 5,069,664 | 12/1991 | Guess et al. . |
| 5,076,276 | 12/1991 | Sakurai et al. . |
| 5,100,423 | 3/1992 | Fearnot . |
| 5,267,954 | 12/1993 | Nita ............................. 604/22 |

FOREIGN PATENT DOCUMENTS

| | | |
|---|---|---|
| 443256 | 12/1990 | European Pat. Off. . |
| 472368 | 2/1992 | European Pat. Off. . |
| 2424733 | 11/1980 | France . |
| 2641693 | 7/1990 | France . |
| 2643272 | 8/1990 | France . |
| 2349120 | 4/1975 | Germany . |
| 2438648 | 2/1976 | Germany . |
| 2453126 | 5/1976 | Germany . |
| 2541919 | 3/1977 | Germany . |
| 2703486 | 12/1977 | Germany . |
| 8119209 | 9/1981 | Germany . |
| 3726210 | 8/1987 | Germany . |
| 3707567 | 9/1987 | Germany . |
| 3707921 | 9/1987 | Germany . |
| 3826414 | 2/1989 | Germany . |
| 3812836 | 4/1990 | Germany . |
| 2453058 | 5/1976 | United Kingdom . |
| 1531659 | 7/1977 | United Kingdom . |
| 1520448 | 6/1987 | United Kingdom . |
| 2208138A | 3/1989 | United Kingdom . |
| 2212267 | 7/1989 | United Kingdom . |
| WO87/01276 | 3/1987 | WIPO . |
| WO87/05793 | 10/1987 | WIPO . |
| WO89/05123 | 6/1989 | WIPO . |
| WO89/06515 | 7/1989 | WIPO . |
| WO89/07419 | 8/1989 | WIPO . |
| WO90/01300 | 2/1990 | WIPO . |
| WO90/07303 | 7/1990 | WIPO . |
| WO91/02489 | 3/1991 | WIPO . |
| WO91/14401 | 10/1991 | WIPO . |
| WO92/11815 | 7/1992 | WIPO . |
| WO92/15253 | 9/1992 | WIPO . |
| 189329 | 7/1986 | European Pat. Off. . |
| 293472 | 11/1986 | European Pat. Off. . |
| 208175 | 1/1987 | European Pat. Off. . |
| 0209468 | 1/1987 | European Pat. Off. . |
| 234951 | 9/1987 | European Pat. Off. . |
| 316796 | 11/1987 | European Pat. Off. . |
| 316796 | 11/1988 | European Pat. Off. . |
| 347098 | 6/1989 | European Pat. Off. . |
| 315290 | 10/1989 | European Pat. Off. . |

ULTRASONIC ABLATION CATHETER DEVICE HAVING ENDOSCOPIC COMPONENT AND METHOD OF USING SAME

RELATED APPLICATION

This patent application is a continuation-in-part of U.S. patent application Ser. No. 07/911,546, entitled ULTRASOUND CATHETER FOR REMOVING OBSTRUCTIONS FROM TUBULAR ANATOMICAL STRUCTURES SUCH AS BLOOD VESSELS and filed on Jul. 9, 1992, now U.S. Pat. No. 5,312,328, which is itself a continuation-in-part of U.S. patent application Ser. No. 07/878,795 entitled ULTRASOUND CATHETER FOR REMOVING OBSTRUCTIONS FROM TUBULAR ANATOMICAL STRUCTURES SUCH AS BLOOD VESSELS and filed on May 5, 1992, now U.S. Pat. No. 5,267,954, which is itself a continuation-in-part of U.S. patent application Ser. No. 07/787,292 entitled ULTRASOUND ABLATION DEVICE ADAPTED FOR GUIDEWIRE PASSAGE and filed on Nov. 4, 1991, now abandoned, which is itself a continuation-in-part of U.S. patent application Ser. No. 07/640,190 entitled INTRAVASCULAR ULTRASONIC ABLATION PROBE and filed on Jan. 11, 1991, now U.S. Pat. No. 5,304,115, the entire disclosures of which are expressly incorporated herein by reference.

FIELD OF THE INVENTION

The present invention relates generally to medical devices and methodology, and more particularly to devices and methodology for removing unwanted matter from tubular anatomical structures such as blood vessels.

BACKGROUND OF THE INVENTION

The use of catheter assemblies to view and clear obstructions from various vessels such as coronary arteries is well known in the prior art. Typically, the occlusion must first be located in a manner which preferably minimizes any resultant trauma to the patient from the location procedure. Once located, angioplasty or other methods may be applied to treat the occluded vessel.

In the treatment of occluded blood vessels, ultrasonic energy has been established as a viable means for removing obstructive matter (e.g., atherosclerotic plaque or thromboemboelic material) therefrom. Examples of ultrasonic devices purportedly useable to remove or ablate vascular obstructions are found in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,935 (Don Michael, et al.) 5,069,664 (Suess, et al.) and 4,920,954 (Alliger, et al.), as well as other patent applications including WO87-05739 (Cooper), WO89006515 (Bernstein, et al.), WO90-0130 (Sonic Needle, Corp.), EP316,789 (Don Michael, et al.), DE 3,821,836 (Schubert), DE 2,438,648 (Pohlman) and EP 0443256A1 (Baruch).

In addition to the foregoing, U.S. patent application Ser. No. 07/640,190 entitled ULTRASONIC ANGIOPLASTY DEVICE INCORPORATING IMPROVED TRANSMISSION MEMBER AND ABLATION PROBE, describes an ultrasound catheter device comprising a flexible tubular catheter having a wire-like elongate ultrasound transmission member which extends longitudinally through the catheter. Ultrasonic energy may be passed through the ultrasound transmission member to effect ultrasonic ablation or destruction of unwanted material located adjacent the distal end of the catheter.

Although the disclosure of U.S. patent application Ser. No. 07/640,190 includes certain configurational and/or material modifications intended to constitute an improvement over other prior art ultrasonic devices, there remains a need in the art for further improvements whereby the ultrasound catheter includes an endoscopic visualization apparatus in addition to the ultrasound ablation apparatus. In this respect, though the transmission of ultrasonic energy through the catheter removes obstructive matter from within the blood vessel, the lack of an endoscopic visualization apparatus in prior art ultrasound ablation catheters necessitates the removal of the catheter from within the blood vessel and the subsequent insertion of an endoscope thereinto to visually evaluate the effect of the ultrasound ablation procedure. As will be recognized, the repeated insertion and removal of separate ultrasound ablation and endoscopic visualization catheters into the blood vessel to properly and completely ablate the occlusive material from therewithin is undesirable due to the resultant trauma to the patient. Thus, a catheter device which incorporates combined ultrasound ablation and endoscopic visualization apparatus would provide the advantage of allowing the response of the occlusive material to the ultrasound catheter intervention to be visually evaluated without having to remove the catheter from within the blood vessel. Additionally, the endoscopic visualization apparatus would aid in identifying plaque or other occlusive materials, and would further facilitate the removal of the unwanted material in a more precise fashion by allowing the distal end of the catheter to be properly positioned adjacent the occlusive material. As such, a catheter device incorporating combined ultrasound ablation and endoscopic visualization apparatus would be operable to examine the real internal results of the catheter intervention in a manner minimizing trauma to the patient, and would identify the areas within the blood vessel which require additional intervention to achieve the desired ablation results.

SUMMARY OF THE INVENTION

The present invention provides an improved ultrasonic catheter device for effecting ultrasonic ablation of unwanted matter within an anatomical passageway, pathway, cavity, blood vessel or organ of a mammalian body. The catheter device further incorporates an endoscopic viewing apparatus whereby the operator of the device may i.) endoscopically visualize the interior of the passageway, pathway, cavity, blood vessel or organ into which the catheter device has been inserted;

ii.) visually verify proper positioning of the distal end of the catheter device relative to the unwanted material; and iii.) visually evaluate whether the unwanted material has been ablated in the desired manner, without the necessity of having to remove the catheter device from within the blood vessel or other passageway.

The catheter device of the present invention comprises an elongate catheter body having proximal and distal ends, and defining at least one lumen extending longitudinally therethrough. Extending longitudinally through the lumen of the catheter body is an ultrasound transmission member, a light transmission member and an optical image transmission member. The proximal end of the ultrasound transmission member or waveguide is connectable to an ultrasound generating device, such as an ultrasound transducer. The proximal end of the light transmission member is connectable to a light source, while the proximal end of the optical image transmission member is connectable to an external image viewing apparatus such as a camera and monitor. The distal ends of the ultrasound transmission member, light transmission member and optical image transmission member are each coupled to a distal head member positioned at the distal end of the catheter body. As such, ultrasonic energy passing through the ultrasound transmission member will result in ultrasonic vibration of the distal head member. Additionally, light from the light source will pass through the light transmission member to the distal end thereof thus illuminating a portion of the vessel lumen, with an optical image passing through the optical image transmission member from the distal end thereof to the external image viewing apparatus.

Additionally, the present invention includes a method of conducting a transluminal intravascular operative procedure utilizing a catheter having at least one lumen extending longitudinally therethrough and including an ultrasound transmission member, a light transmission member and an optical image transmission member extending longitudinally through the lumen. Subsequent to inserting the catheter into a blood vessel, the light transmission member and optical image transmission member are activated to aid in properly positioning the distal head member of the catheter adjacent the occlusive material in the vessel. Once the distal head member has been properly positioned and the light transmission member and optical image transmission member deactivated, ultrasonic energy is passed through the ultrasound transmission member to ablate the occlusive material. When the transmission of ultrasonic energy through the ultrasound transmission member is stopped, the light transmission member and optical image transmission member are re-activated to visually determine if the occlusive material has been completely ablated. The aforementioned steps may be repeated as necessary to completely ablate the occlusive material.

Further and more specific aspects of the present invention will become apparent to those skilled in the art upon reading and understanding the following detailed description of the preferred embodiment, and the accompanying drawings.

BRIEF DESCRIPTION OF THE DRAWINGS

These as well as other features of the present invention will become more apparent upon reference to the drawings wherein:

FIG. 3a is a cross-sectional view through line 4—4 of FIG. 3;

DETAILED DESCRIPTION OF THE PREFERRED EMBODIMENT

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments that are also intended to be encompassed within the spirit and scope of the invention.

Figure 1:
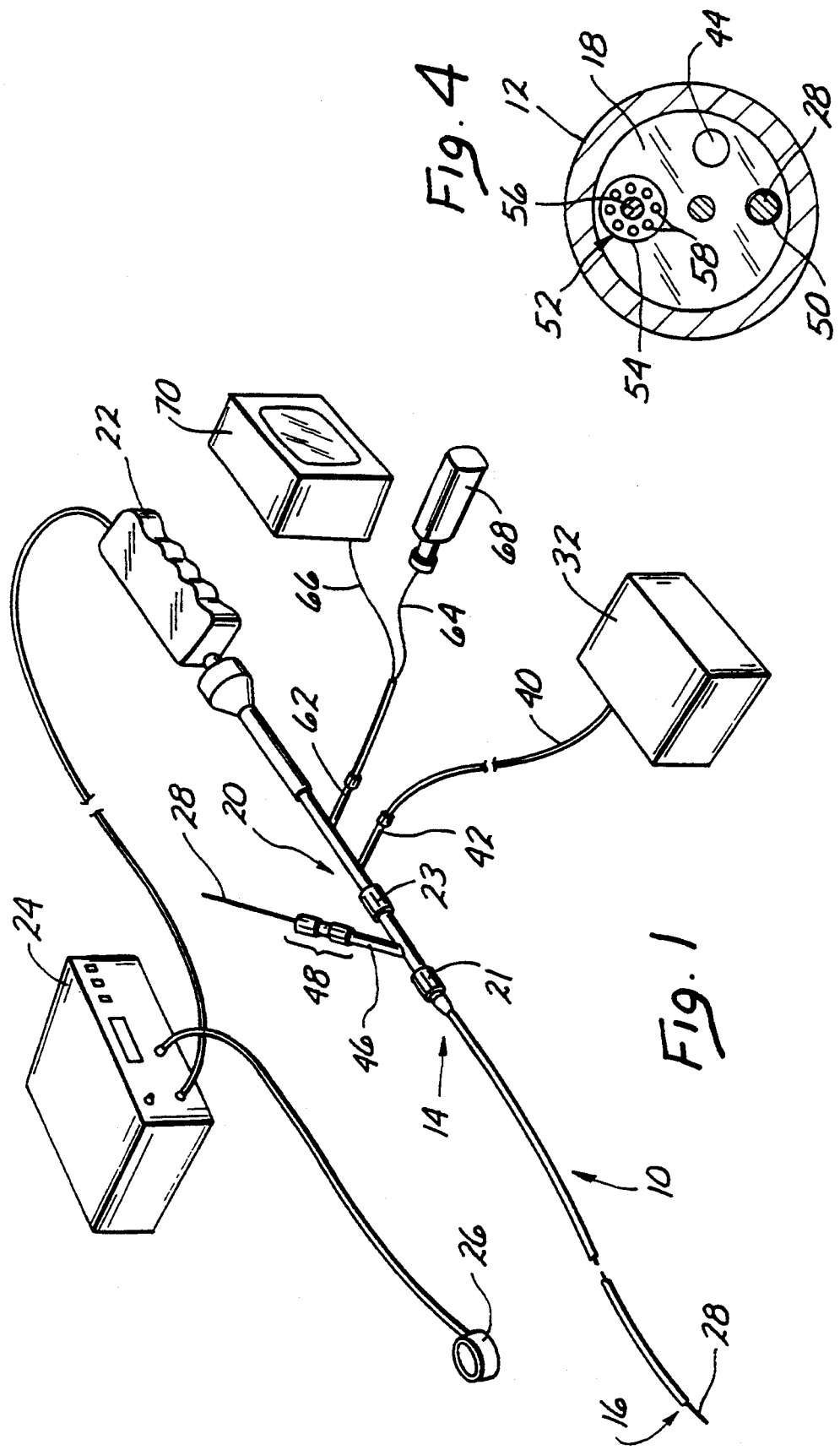
FIG. 1 is a perspective view of a catheter device incorporating combined ultrasound ablation and endoscopic visualization apparatus.

Referring now to the drawings, FIG. 1 perspectively illustrates an ultrasonic catheter device 10 which is constructed in accordance with the preferred embodiment of the present invention and incorporates combined ultrasound ablation and endoscopic visualization components. In the preferred embodiment, the catheter device 10 comprises an elongate catheter body 12 having a proximal end 14, a distal end 16, and defining a single lumen 18 extending longitudinally therethrough. The ultrasound catheter device 10 is operatively coupled, by way of a proximal connector assembly 20, to an ultrasound transducer 22 (Model UAT-1000, Baxter Healthcare Corporation, Edwards Less Invasive Surgery Division, 17221 Redhill Avenue, Irvine, Calif. 92714). The ultrasound transducer 22 is connected to a signal generator 24 (Model UAG-1110, Baxter Healthcare Corporation, Edwards Less Invasive Surgery Division, 17221 Redhill Avenue, Irvine, Calif. 92714). The signal generator 24 is provided with a foot actuated on-off switch 26. When the foot actuated on-off switch 26 is depressed, the signal generator 24 sends an electrical signal to the ultrasound transducer 22. The ultrasound transducer 22 then converts the electrical signal to ultrasonic energy. Such ultrasonic energy subsequently passes through the catheter device 10 of the present invention, thereby being delivered to the distal end 16 of the catheter body 12. A guidewire 28 may be utilized in conjunction with the catheter device 10, as will be more fully described below.

Figure 2:
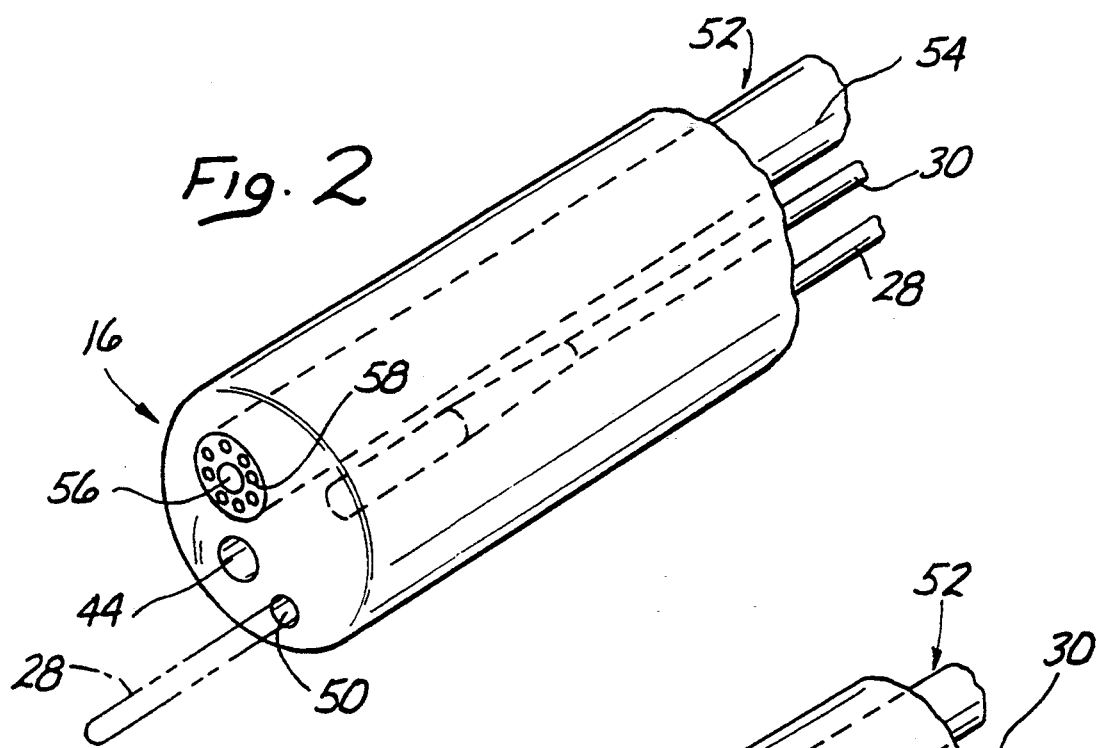
FIG. 2 is a partial enlarged perspective view of the distal end of an embodiment of an over-the-wire catheter of the present invention.
Figure 4A:
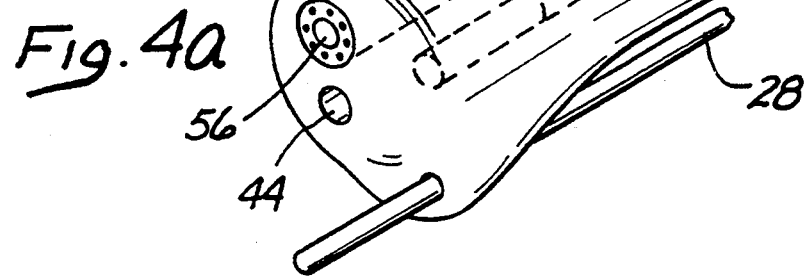
FIG. 4 is a partial enlarged perspective view of the distal end of an embodiment of a monorail catheter of the present invention.
Figure 3:
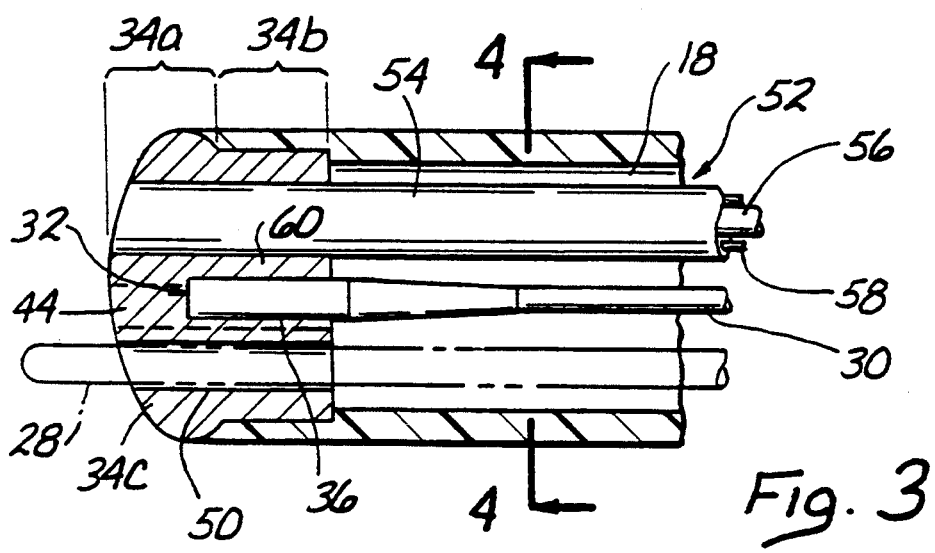
FIG. 3 is a longitudinal sectional view of the distal end of the catheter as shown in FIG. 2.

The distal end 16 of the catheter body 12 of the catheter device 10 is shown, in detail, in FIGS. 2, 3 and 4. In the preferred embodiment, the catheter body 12 is formed of a flexible plastic material such as nylon (Pebax ™) manufactured by Atochimie, Cour be Voie, Hauts VeSine, FRANCE. The flexible catheter body 12 is preferably in the form of an elongate tube having one or more lumens extending longitudinally therethrough. However, as previously explained, in the preferred embodiment of the present invention only a single lumen 18 extends longitudinally through the tubular catheter body 12. Extending longitudinally through the lumen 18 of the catheter body 12 is an elongate ultrasound transmission member 30 or waveguide having a proximal end which is connectable to the ultrasound transducer 22 such that ultrasonic energy will pass through the ultrasound transmission member 30. As such, when the foot actuated on-off switch 26 operatively connected to the ultrasound transducer 22 is depressed, ultrasonic energy will pass through the ultrasound transmission member 30 to the distal end 32 thereof and, hence, the distal end 16 of the catheter body 12. More particularly, the ultrasound transmission member 30 serves to transmit the ultrasonic energy from the proximal connector assembly 20 to a distal head 34 mounted on the distal end 16 of the catheter body 12.

The distal head 34 comprises a substantially rigid member affixed to the distal end 16 of the catheter body 12. In the embodiment shown, the distal head 34 comprises a generally frusto-conical distal portion 34a, and a generally cylindrical proximal portion 34b. The proximal portion 34b of the distal head 34 is inserted into the open distal end 16 of the catheter body 12, as shown. The outer diameter of the proximal portion 34b of the distal head 34 is approximately the same as or slightly less than the inner diameter of the lumen 18 of the catheter body 12 such that the proximal portion 34b may be inserted into the distal end 16 of the catheter body 12 to a point whereat the distal portion 34a of the distal head 34 abuts the catheter body 12. Preferably, the outer diameter of the distal portion 34a is approximately the same as the outer diameter of the catheter body 12, thereby forming a generally smooth outer surface at the juncture of the distal head 34 and the catheter body 12, as shown in FIGS. 2 and 3.

The distal head 34 is firmly bonded, attached, or connected to the catheter body 12 such that the distal head 34 is prevented from undergoing longitudinal or transverse movements separate from or relative to the catheter body 12. Such affixation of the distal head 34 to the catheter body 12 increases the conveyance of ultrasound energy into the distal end 16 thereof, thereby resulting in enhanced cavitation effects created by the distal end 16 of the catheter body 12. Such bonding connection or attachment of the distal head 34 to the catheter body 12 may be accomplished by any suitable member. One means of attaching the distal head 34 to the catheter body 12 is through the use of an adhesive which is applied to the outer surface of the proximal portion 34b of the distal head 34 prior to the insertion thereof into the distal end 16 of the catheter body 12. The adhesive may comprise any suitable adhesive, such as cyanoacrylate (e.g., Loctite TM Corp., Ontario, Canada or Aron Alpha TM, Borden, Inc., Columbus, Ohio) or polyurethane (e.g., Dymax TM, Dymax Engineering Adhesive, Torrington, Conn.) to firmly bond and attach the distal head 34 to the catheter body 12. The distal head 34 may be formed of any suitable rigid material, such as metal or plastic. The distal head 34 is preferably formed of radiodense material so as to be easily discernible by radiographic means. Accordingly, the distal head 34 may preferably be formed of metal or, alternatively, may be formed of plastic, ceramic, or rubber materials, optionally having one or more radiodense markers affixed thereto or formed therein. For example, the distal head 34 may be molded of plastic, such as acrylonitrile-butadine-styrene (ABS) and one or more metallic foil strips or other radiopaque markers may be affixed to such plastic distal head 34 in order to impart sufficient radiodensity to permit the distal head 34 to be readily located by radiographic means. Additionally, in embodiments wherein the distal head 34 is formed of molded plastic or other non-metallic material, a quantity of radiodense fillers, such as powdered Bismuth or Barium Sulfate ($BaSO_4$) may be disposed within the plastic or other non-metallic material of which the distal head 34 is formed so as to impart enhanced radiodensity thereto.

In devices wherein the distal head 34 is formed of plastic, the surrounding catheter body 12 may be thoroughly welded, heat sealed, or solvent welded to the plastic distal head 34, in accordance with the types of plastics employed. In the alternative to the use of adhesives, various mechanical or frictional connectors, such as screw threads, lugs, or other surface modifications formed on the proximal portion 34b of the distal head 34, may be utilized to hold the distal head 34 in a fixed position relative to the distal end 16 of the catheter body 12. In such embodiments, corresponding grooves, detents, or surface modifications may also be formed in the surrounding innerluminal surface of the catheter body 12 so as to cooperate with any such threads, lugs, or other surface modifications formed on the opposing surface of the distal head 34. Such threads, lugs, or other surface modifications will be configured and constructed as to mechanically or frictionally hold the distal head 34 in fixed position relative to the catheter body 12.

As best seen in FIG. 3, the ultrasound transmission member 30 is inserted into a bore 36 which extends longitudinally into the proximal portion 34b of the distal head 34. The distal end 32 of the ultrasound transmission member 30 is then firmly held within the bore 36 by the frictional engagement thereof to the surrounding material of the distal head 34, or by other mechanical or chemical affixation means such as weldments, adhesive, etc. Firm affixation of the ultrasound transmission member 30 to the distal head 34 serves to facilitate direct transmission of the quanta of ultrasonic energy passing through the ultrasound transmission member 30 to the distal head 34. As a result, the distal head 34, and a distal portion of the tubular catheter body 12, are caused to undergo ultrasonic vibration in accordance with the combined quanta of ultrasonic energy being transmitted through the ultrasound transmission member 30.

In the preferred embodiment, the ultrasound transmission member 30 may be formed of any material capable of effectively transmitting the ultrasonic energy from the ultrasound transducer 22 to the distal head 34, including but not necessarily limited to metal, plastic, hard rubber, ceramic, and/or composites thereof. In accordance with one aspect of the invention, all or a portion of the ultrasound transmission member 30 may be formed of one or more materials which exhibit superelasticity. Such materials should preferably exhibit super-elasticity consistently within the range of temperatures normally encountered by the ultrasound transmission member 30 during operation of the catheter device 10. Specifically, all or part of the ultrasound transmission member 30 may be formed of one or more metal alloys known as "shape member alloys".

Examples of super-elastic metal alloys which are usable to form the ultrasound transmission member 30 of the present invention are described in detail in U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are super-elastic within the temperature range at which the ultrasound transmission member 30 of the present invention operates, any and all of which superelastic metal alloys may be usable to form the super-elastic ultrasound transmission member 30.

In particular, one presently preferred super-elastic metal alloy of which the ultrasound transmission member 30 may be formed is a nickel-titanium alloy wire made up of 55.8% nickel (NiTi containing 55.8% weight percent NiTi). Such material is commercially available as Tinel ™ wire from Raychem Corporation, Menlo Park, Calif.

| Properties of NiTi Alloy Having 50.8 At. % Nickel/Balance Titanium | | |
| --- | --- | --- |
| Property* | Units | Value |
| Superelastic Temperature Range | °C. | 20 to 80 |
| Loading Plateau Stress (at 20° C.) | MPa | 480 |
| Unloading Plateau Stress | Mpa | 135 |
| Permanent Set (at 20° C. after 8% strain) | % | 0.2 |
| Ultimate Tensile Strength (at 20° C.) | MPa Ksi | 1150 170 |
| Elongation at Failure | % | 10 |
| Melting Point | °C. | 1350 |
| Density | g/cm lbs/cu. Inch | 6.5 0.235 |

*Typical Values for Cold Worked and Shape Set Condition

As will be recognized, in any embodiment of the present invention, the ultrasound transmission member 30 may be tapered, narrowed, or otherwise reduced in cross-sectional dimension within the catheter device 10 so as to decrease the rigidity of the ultrasound transmission member 30 and/or to cause amplification of the ultrasound transmitted to and from the distal end 32 thereof. As seen in FIG. 3, the distal end 32 of the ultrasound transmission member 30 received into the bore 36 is preferably enlarged to facilitate greater efficiency in the transmission of ultrasound energy from the ultrasound transmission member 30 to the distal head 34.

The proximal connector assembly 20 of the catheter device 10 comprises an elongate, rigid body defining frontal, mid and rear portions. The frontal portion of the body is firmly connected to the proximal end 14 of the catheter body 12 via a threaded gripping member 21 engaged thereto. In this respect, the proximal end 14 of the catheter body 12 preferably has a flared configuration and includes an annular flange formed on the outermost end thereof which is brought into sealed engagement with the proximal connector assembly 20 when the gripping member 21 is threadably engaged to the body. The proximal end of the frontal portion is connected to the distal end of the mid-portion of the body via a second gripping member 23. As will be recognized, to facilitate the aforementioned construction, threads are formed on the distal ends of the frontal and mid-portions of the proximal connector assembly 20. The extreme proximal end of the rear portion of the proximal connector assembly 20 is provided with a sonic connector assembly or apparatus which is configured to effect operative attachment of the proximal end of the ultrasound transmission member 30 to the horn of the ultrasound transducer 22. A more thorough description of the manner and apparatus used to facilitate the operative attachment of the ultrasound transmission member 30 to the ultrasound transducer 22 is set forth in U.S. patent application Ser. No. 07/911,546, the entire disclosure of which is hereby expressly incorporated herein by reference.

In the present invention, an injection pump 38 is connected, by way of an infusion tube 40, to an infusion port or sidearm 42 in the mid-portion of the proximal connector assembly 20. The injection pump 38 is used to infuse coolant fluid (e.g., 0.9% NaCl solution) into and/or through the catheter device 10, and more particularly into the lumen 18 of the catheter body 12. Such flow of coolant fluid may be utilized to prevent overheating of the ultrasound transmission member 30 extending longitudinally through the lumen 18. Due to the desirability of infusing coolant fluid into the catheter body 12, extending longitudinally through the distal head 34 is at least one fluid outflow aperture 44 which permits the coolant fluid to flow from the lumen 18 out of the distal end 16 of the catheter body 12. Such flow of the coolant fluid through the lumen 18 serves to bathe the outer surface of the ultrasound transmission member 30, thereby providing for an equilibration of temperature between the coolant fluid and the matter of the ultrasound transmission member 30. Thus, the temperature and/or flow rate of coolant fluid may be adjusted to provide adequate cooling and/or other temperature control of the ultrasound transmission member 30.

In addition to infusing coolant fluid into and/or through the catheter device 10, the injection pump 38 may alternatively be utilized to infuse irrigation fluid into the lumen 18 of the catheter body 12 for purposes of removing debris from within the vessel lumen and/or forming a fluidic column to remove blood from the region of the distal head 34 and enhance the image transmitted by the endoscopic visualization apparatus incorporated into the catheter device 10 as will hereinafter be described. The creation of a fluidic column flowing distally from the distal head 34 also facilitates the ablation of occlusive material via a cavitation effect wherein ultrasonic energy is transmitted to the occlusive material as waves which are propagated through the fluidic column. As such, in the catheter device 10, occlusive material may be ablated by direct contact of the distal head 34 therewith, or alternatively by the aforementioned cavitation effect. As will be recognized, for the cavitation effect to occur, the fluidic column must necessarily be formed by a liquid medium infused into the catheter device 10 by the injection pump 38.

In additon to the foregoing, the injection pump 38 may be utilized to infuse a radiographic contrast medium into the catheter device 10 for purposes of checking the patency of the vessel during a radiographic imaging procedure. Examples of iodinated radiographic contrast media which may be selectively infused into the catheter device 10 via the injection pump 38 are commercially available as Angiovist 370 from Berlex Labs, Wayne, N.J. and Hexabrix from Malinkrodt, St. Louis, Mo.

Formed on and extending outwardly from the frontal portion of the proximal connector assembly 20 is a guidewire insertion sidearm 46 for receiving the transluminal body guidewire 28. The guidewire insertion sidearm 46 includes a hollow bore extending therethrough which communicates with the bore of the proximal connector assembly 20. A guidewire gripping/sealing apparatus 48 may be mounted on the guidewire insertion sidearm 46 to grasp and hold the guidewire 28 in a fixed longitudinal position relative to the catheter device 10 and to provide a seal to prevent the backflow of blood through the catheter device 10. Examples of guidewire gripping/sealing apparatus 48 which may be utilized in this application include those which are available commercially as Product Nos. 1905017A and 1905014A from Medical Disposables International, West Conshocken, Pa.

The distal head 34 is provided with a guidewire passage aperture 50 which extends longitudinally therethrough. The guidewire passage aperture 50 is preferably formed through the distal head 34 at a location inboard of the catheter body 12 such that the guidewire 28 may pass therethrough into the lumen 18 of the catheter body 12. This embodiment of the catheter device 10 wherein the guidewire 28 passes through the guidewire passage aperture 50 and into the lumen 18 of the catheter body 12 constitutes an "over-the-wire" embodiment of the present invention. Additionally, the guidewire passage aperture 50 may be sized so as to be slightly larger than the outer diameter of the guidewire 28 to be passed therethrough so as to permit the coolant fluid infused into the lumen 18 to pass out of the guidewire passage aperture 50, even when the guidewire 28 is extending therethrough, in addition to the fluid outflow aperture 44. The catheter device 10 may, thus, be advanced and/or retracted over a pre-positioned guidewire in accordance with typical operative technique utilized in interventional cardiology procedures such as percutaneous transluminal angioplasty procedures.

Alternatively, as seen in FIG. 4, the distal head 35 may be formed such that a portion of the distal head extends laterally outboard of the outer surface of the catheter body 12 and the guidewire passage aperture 50a may be, likewise, positioned outboard of the outer surface of the catheter body 12 such that the guidewire 28 extends along side the catheter body 12 and through the guidewire passage aperture 50a. This embodiment of the invention wherein the guidewire 28 is passed outboard of the outer surface of the catheter body 12 and through the guidewire passage aperture 50a constitutes a "monorail" embodiment of the present invention.

As previously explained, coolant fluid may be circulated through the lumen 18 to bathe the outer surface of the ultrasound transmission member 30, thereby providing a desired equilibration of temperature. In this respect, the temperature and flow rate of the coolant fluid may be specifically controlled to maintain the temperature of the ultrasound transmission men,her 30 at a desired temperature within its optimal working range. In particular, in embodiments of the invention wherein the ultrasound transmission member 30 is formed of a metal alloy which exhibits optimal physical properties (e.g., superelasticity) within a specific range of temperatures, the temperature and flow rate of the coolant fluid infused into the sidearm 42 may be specifically controlled to maintain the temperature of the ultrasound transmission member 30 within the range of temperatures at which it demonstrates the most desirable physical properties. For example, in embodiments of the invention wherein the ultrasound transmission member 30 is formed of a shape memory alloy which exhibits superelasticity when in its martensite state, but which loses superelasticity as it transitions to an austenite state, it will be desirable to adjust the temperature of the coolant fluid infused through the sidearm 42 so as to maintain the shape memory alloy of the ultrasound transmission member 30 within a temperature range at which the alloy will remain in its martensite state and will not transition to an austenite state. The temperature at which such shape memory alloys transition from a martensite state to an austenite state is known as the "martensite transition temperature" (Ms) of the material. Thus, in these embodiments, the coolant fluid infused through the sidearm 42 will be at such temperature and will be infused at such rate, as to maintain the shape memory alloy of the ultrasound transmission member 30 below its martensite transition temperature (Ms).

In addition to the ultrasound ablation apparatus as previously described, the catheter device 10 also incorporates endoscopic visualization apparatus. In the preferred embodiment, the visualization apparatus comprises an elongate transmission member 52 extending longitudinally therethrough the lumen 18 of the catheter body 12. The transmission member 52 comprises a tubular outer sheath 54 having at least one image transmitting optical fiber bundle 56 extending longitudinally therethrough. The image transmitting optical fiber bundle 56 is encircled by a multiplicity of light transmitting optical fiber bundles 58 of smaller diameter, which also extend longitudinally through the outer sheath 54. As such, both the image transmitting optical fiber bundle 56 and light transmitting optical fiber bundles 58 extend along the entire length of the transmission member 52 to the distal end thereof and are encased in the outer sheath 54 which serves to protect the integrity of the optical fiber bundles 56, 58.

As best seen in FIG. 3, the distal end of the transmission member 52 is inserted into a bore 60 which extends longitudinally through the distal head 34. The distal end of the transmission member 52 is firmly held within the bore 60 by frictional engagement to the surrounding material of the distal head 34, or by other mechanical or chemical affixation means. In this respect, the distal end of the transmission member 52 is preferably held within the bore 60 via the utilization of an adhesive which is applied to the distal region of the outer surface of the sheath 54 prior to the insertion of the transmission member 52 into the bore 60. Disposed on the distal end of the transmission member 52 is an optic lens which is a glass gradient index lens bonded to the distal ends of the image transmitting and light transmitting optical fiber bundles 56, 58 by an acrylic ester ultraviolet cured adhesive.

As best seen in FIG. 3, the lens preferably has an arcuate configuration such that when the distal end of the transmission member 52 is extended through and held firmly within the bore 60, the lens is substantially continuous with the arcuately contoured outer surface 34c of the distal portion 34a of the distal head 34. As such, when the transmission member 52 is properly engaged to the distal head 34, the light transmitting optical fiber bundles 58 are operable to transmit light from the proximal end of the transmission member 52 beyond the distal end 16 of the catheter device 10 to illuminate an object of interest. Additionally, the image transmitting optical fiber bundle 56 is able to transmit light received by the lens back to the proximal end of the transmission member 52. The image and light transmitting optical fiber bundles 56, 58 are preferably comprised of silica optical fibers, though other materials may alternatively be utilized.

In the present invention, the distal end of the transmission member 52 need not include a separate lens bonded thereto. In this respect, the distal end of the transmission member 52, and hence the distal ends of the image and light transmitting optical fiber bundles 56, 58, may be polished rather than having the lens bonded thereto. As will be recognized, when the distal end of the transmission member 30 is polished rather than having a lens affixed thereto, the transmission member 52 is cut in a manner wherein the polished distal end thereof will be substantially continuous with the arcuately contoured outer surface 34c of the distal portion 34a when the transmission member 52 is extended through and held firmly within the bore 60.

As previously explained, the distal end of the transmission member 52 is extended through the distal head 34 in a manner wherein the lens is substantially continuous with the outer surface 34c of the distal head 34. The proximal end of the transmission member 52 extends from a sidearm 62 formed on the mid-portion of the proximal connector assembly 20 and is preferably separated into two sections consisting of a first section 64 through which the light transmitting optical fiber bundles 58 are extended, and a second section 66 through which the image transmitting optical fiber bundle 56 is extended. The first section 64, and, hence, the proximal ends of the light transmitting optical fiber bundles 58, are operatively connected to a light source 68 which may be selectively activated to transmit light through the light transmitting optical fiber bundles 58 to the distal end of the transmission member 52. The second section 66, and, hence, the proximal end of the image transmitting optical fiber bundle 56, is operatively connected to an integrated camera and monitor apparatus 70 which allows an image from the distal end 16 of the catheter device 10 to be observed when the light source 68 is activated. However, it will be recognized that the camera and monitor may be provided as separate components which are operatively coupled to the image transmitting optical fiber bundle 56 at any location along the catheter device 10. As previously explained, the proximal end of the ultrasound transmission member 30 is operatively connected via the sonic connector on the rear portion of the proximal connector assembly 20 to the ultrasound transducer 22.

Due to the inclusion of the ultrasound transmission member 30 and the endoscopic transmission member 52, the catheter device 10, when advanced into a vessel with occlusive material, can be used to visually identify the internal structure of the vessel. In this respect, if it is determined that it is necessary to ablate unwanted material in the vessel, ultrasonic energy may be selectively transmitted through the ultrasound transmission member 30 to conduct the ablation process. After the ablation process is conducted, the effects of the intervention may be visually evaluated without the necessity of having to remove the catheter device 10 from within the vessel. As such, the onboard angioscopic imaging component of the catheter device 10, in addition to facilitating the identification of the unwanted material and the positioning of the distal head 34 adjacent thereto, also allows the manner in which the occlusive material responds to catheter intervention to be visually evaluated. Accordingly, unwanted material can be removed more precisely from within the vessel, with the capacity also being provided to examine real internal results of intervention as well as identify the areas where a blood vessel needs additional intervention to achieve the desired ablation results.

A more detailed description of a preferred method of conducting a transluminal intravascular operative procedure utilizing the catheter device 10 of the present invention is described in relation to FIGS. 5a–5e. In the initial step of the preferred method, the catheter body 12 of the catheter device 10 is inserted into a blood vessel 72 or other organ. As the catheter body 12 is being inserted into the vessel 72, the light source 68 and camera/monitor apparatus 70 are preferably activated so as to transmit optical images from the distal end 16 of the catheter body 12 to the operator. Advantageously, the angioscopic imaging allows the distal head 34 to be positioned directly adjacent the unwanted occlusive material 74 within the blood vessel 72, as well as aid in identifying the occlusive material 74. After the distal head 34 has been properly positioned adjacent the occlusive material 74, the light source 68 and camera/monitor apparatus 70 are deactivated and the on-off switch 26 depressed thereby causing ultrasonic energy to be transmitted from the ultrasound transducer 22 to the distal head 34 via the ultrasound transmission member 30. The transmission of the ultrasonic energy through the ultrasound transmission member 30 ablates the occlusive material 74 in the manner shown in FIG. 5b.

Figure 5A:
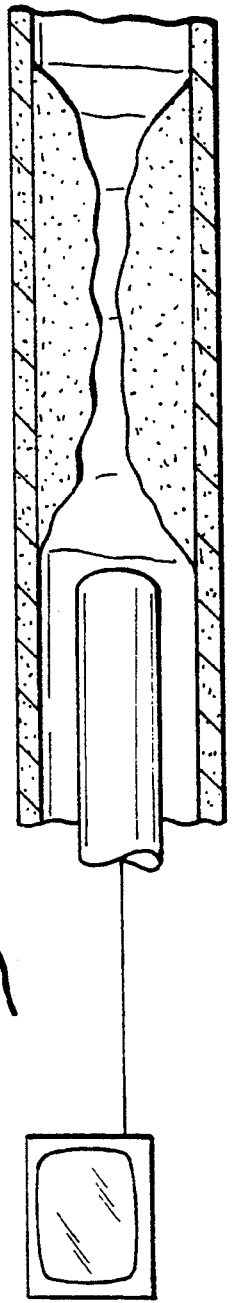
FIGS. 5a-5e are illustrations of the sequence of steps of a preferred method of utilizing the catheter of the present invention.
Figure 5B:
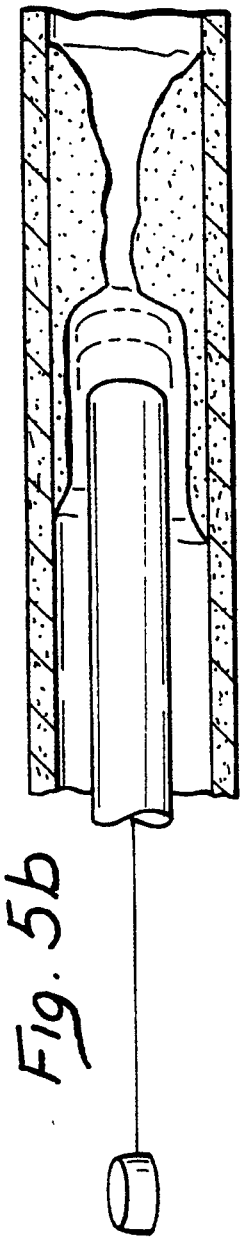
Figure 5C:
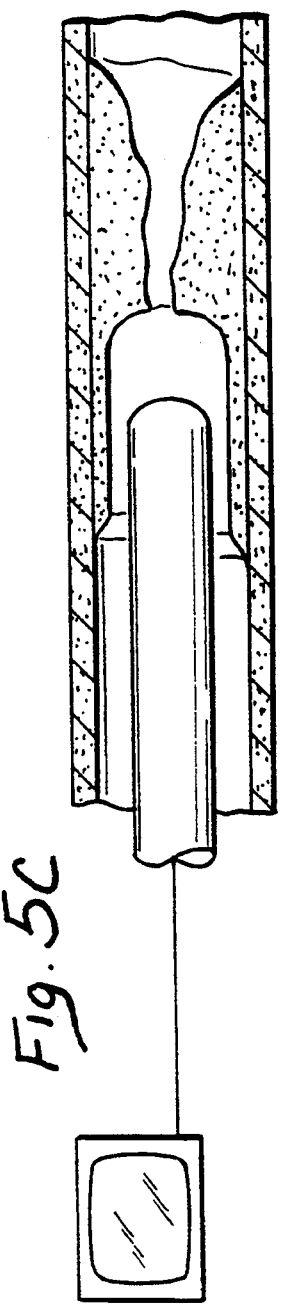
Figure 5D:
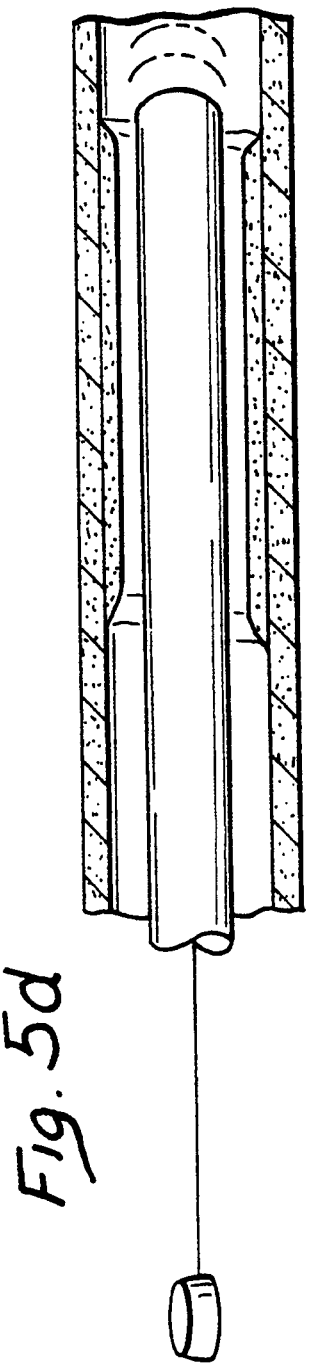
Figure 5E:
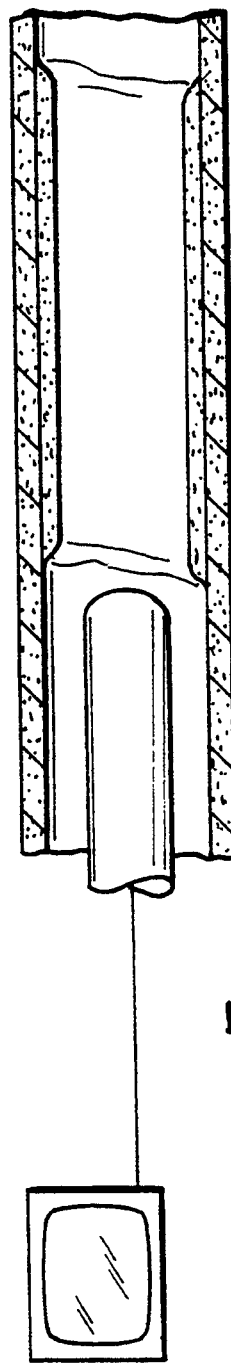

After the ablation process has been conducted for a desired period of time, the transmission of ultrasonic energy through the ultrasound transmission member 30 is stopped, with the light source 68 and camera/monitor apparatus 70 being re-activated to allow the efficacy of the ablation process to be visually evaluated. If it is determined that the occlusive material 74 has been completely ablated, the catheter body 12 of the catheter device 10 is withdrawn from within the blood vessel 72. However, if it is determined that the occlusive material 74 has only been partially ablated as seen in FIG. 5c, the light source 68 and camera/monitor apparatus 70 are once again deactivated, with the on-off switch 26 being depressed to facilitate the transmission of ultrasonic energy through the ultrasound transmission member 30 to complete the ablation process, as seen in FIG. 5d. Thereafter, the transmission of ultrasound energy through the ultrasound transmission member 30 is once again stopped, with the light source 68 and camera/monitor apparatus 70 being re-activated to permit a second visual evaluation to determine whether the occlusive material 74 has been completely ablated from within the blood vessel 72, as seen in FIG. 5e. As will be recognized, the aforementioned steps may be repeated as is necessary to completely ablate the occlusive material 74.

Although the invention has been described herein with specific reference to presently preferred embodiments thereof, it will be appreciated by those skilled in the art that various additions, modifications, deletions and alterations may be made to such preferred embodiments without departing from the spirit and scope of the invention. Accordingly, it is intended that all reasonably foreseeable additions, deletions, alterations and modifications be included within the scope of the invention as defined in the following claims.

What is claimed is:

1. A catheter device insertable into a body lumen and incorporating combined ultrasound ablation and endoscopic visualization apparatus, said device comprising:
   an elongate catheter body having a proximal end and a distal end;
   an ultrasound transmission member extending longitudinally through said catheter body, said ultrasound transmission member having a proximal end and a distal end, the proximal end of said ultrasound transmission member being connectable to an ultrasound transducer such that ultrasonic energy will pass through said ultrasound transmission member to said distal end thereof;

a distal head member affixed to said distal end of said catheter body, said distal end of said ultrasound transmission member being coupled to said distal head member such that said distal head member will vibrate when ultrasonic energy is transmitted through said ultrasound transmission member;

a light transmission member extending longitudinally through said catheter body, said light transmission member having a proximal end and a distal end, said proximal end of said light transmission member being connectable to a light source such that light will pass through said light transmission member to said distal end thereof; and an optical image transmission member extending longitudinally through said catheter body, said optical image transmission member having a proximal end and a distal end, said proximal end of said optical image transmission member being connectable to an external image viewing apparatus such that an optical image will pass through said optical image transmission member from said distal end thereof to said external image viewing apparatus.

2. The device of claim 1 wherein said distal head member comprises a distal portion defining an arcuate outer surface and a generally cylindrical proximal portion, said proximal portion being affixed to said distal end of said catheter body.

3. The device of claim 2 wherein said light transmission member and said optical image transmission member comprise a single, elongate transmission member extending longitudinally through said catheter body, said light and optical image transmission member comprising an outer sheath having an image transmitting optical fiber bundle encircled by a multiplicity of light transmitting optical fiber bundles of smaller diameter extending longitudinally therethrough, said light and optical image transmission member having a proximal end and distal end, said proximal end of said light and optical image transmission member being connectable to said external image viewing apparatus and said light source.

4. The device of claim 3 wherein said distal end of said light and optical image transmission member is arcuately configured and extended through a bore extending longitudinally through said distal head member and held therein in a manner wherein said distal end is substantially continuous with said arcuate outer surface of said distal portion.

5. The device of claim 4 wherein said distal end of said light and optical image transmission member includes an arcuately configured lens thereon, said distal end of said light and optical image transmission member being extended through and held within said bore in a manner wherein said lens is substantially continuous with said arcuate outer surface of said distal portion.

6. The device of claim 2 wherein said distal end of said ultrasound transmission member is inserted into and held within a bore extending longitudinally within said proximal portion of said distal head member.

7. The device of claim 2 wherein said distal head member further includes a guidewire passage aperture extending longitudinally therethrough.

8. The device of claim 7 wherein said guidewire passage aperture is communicative with said at least one lumen of said catheter body such that a guidewire may concomitantly pass through said at least one lumen of said catheter body and through said guidewire passage aperture.

9. The device of claim 7 wherein said distal head member includes a guidewire support portion protruding laterally outboard of the outer surface of said catheter body, said guidewire passage aperture extending longitudinally through said guidewire support portion generally parallel to the longitudinal axis of said catheter body such that said guidwire may be passed next to said catheter body and through said guidewire passage aperture.

10. The device of claim 2 wherein said distal head member further includes at least one fluid outflow aperture extending longitudinally therethrough.

11. The device of claim 1 wherein said light transmission member comprises at least one optical fiber bundle.

12. The device of claim 1 wherein said optical image transmission member comprises at least one optical fiber bundle.

13. The device of claim 1 wherein said ultrasound transmission member is formed of a superelastic metal alloy.

14. The device of claim 13 wherein said superelastic metal alloy is NiTi.

15. The device of claim 1 wherein said catheter body defines at least one lumen extending longitudinally therethrough, said ultrasound transmission member, said light transmission member and said optical image transmission member extending longitudinally through said lumen.

* * * * *